United States Patent [19]
David et al.

[11] 3,999,857
[45] Dec. 28, 1976

[54] REFRACTIVE INDEX DETECTOR

[75] Inventors: Donald J. David, Centerville, Ohio; David A. Shaw, Pittsfield, Ill.; Huel C. Tucker, Centerville, Ohio

[73] Assignee: Monsanto Research Corporation, St. Louis, Mo.

[22] Filed: May 29, 1975

[21] Appl. No.: 582,064

[52] U.S. Cl. .............................. 356/133; 356/131
[51] Int. Cl.² ....................................... G01N 21/46
[58] Field of Search .......... 356/131, 132, 133, 135, 356/136, 137

[56] References Cited
UNITED STATES PATENTS

| | | | |
|---|---|---|---|
| 2,569,127 | 9/1951 | Eltenton | 356/133 |
| 2,885,923 | 5/1959 | Simmons | 356/136 |
| 3,017,802 | 1/1962 | Witt | 356/133 |
| 3,370,502 | 2/1968 | Wilks | 356/133 |
| 3,520,619 | 7/1970 | Ward | 356/133 |

*Primary Examiner*—John K. Corbin
*Assistant Examiner*—Richard A. Rosenberger
*Attorney, Agent, or Firm*—Bruce Stevens

[57] ABSTRACT

A refractive index detector is described comprising a waveguide, means for contacting said waveguide with a fluid, a light source and means to transmit light into said waveguide, means for detecting light exiting from said waveguide as an indication of the refractive index of said fluid and means to automatically change the angle of incidence of the light entering said waveguide in response to changes of refractive index of said fluid. A preferred embodiment of the detector for use as a detector for gradient elution chromatography has means to indicate the rate of change of refractive index. A preferred means to automatically change the angle of incidence of the light entering the waveguide is a movable prism. It is preferred to use a monochromatic light source in the detector. It is preferred to provide reference means for the detector to compensate for changes in intensity of the light output from said light source. A process for determining the refractive index of effluent from a gradient elution liquid chromatograph is described comprising continuously measuring the differential of the refractive index of said effluent to compensate for the change in refractive index resulting from the continuously changing composition of the elution solution.

7 Claims, 9 Drawing Figures

REFRACTIVE INDEX DETECTOR

BACKGROUND OF THE INVENTION

1. Field of the Invention

The invention relates to fiber-optics refractive index detecting devices and the use of such devices as detectors in liquid chromatography.

2. Description of the prior art

U.S. Pat. No. 2,569,127 describes a fiber-optics apparatus designed to continuously measure and record the refractive index of a fluid substance, and to control the properties or characteristics of the fluid in response to variations in refractive index.

U.S. Pat. No. 2,964,993 describes a fiber-optics apparatus for automatically measuring specific gravity and/or composition of a fluid which apparatus relies on the changes in the conductivity of light passing through a radiant energy guide, such as an artificial sapphire rod, as a consequence of changes in the absorption characteristics and index of refraction. The apparatus has a null balanced indicator which operates by changing the position of the light source along the waveguide.

U.S. Pat. No. 3,017,802 describes a fiber-optics apparatus which measures the index of refraction and absorption characteristics of a substance surrounding a radiant energy guide or rod member and provides for the measurement also of a reference fluid.

U.S. Pat. No. 3,311,014 describes a fiber-optics apparatus which provides a unitary light-to-electrical voltage transforming apparatus for selectively adjusting the entry angle at which the central longitudinal axis of the light cone enters an edge portion of one end of a light transmitting fluid immersed probe so that only one probe need be used to measure many different index of refraction ranges of fluids. A reference cell is provided to maintain at a set value the intensity of the light transmitted to the probe.

U.S. Pat. No. 3,370,502 describes a fiber-optics absorption cell having a rod with a cell surrounding the rod, radiant energy directed at one end of the rod and passing down the rod with frustrated multiple internal reflection. The rod may have its effective length adjustable so as to permit nulling or calibration.

U.S. Pat. No. 3,513,319 describes a fiber-optics refractometer comprising a bundle of radiation transparent tubes extending from a radiation source to a detector. The central section of the tubes extend through a vessel which contains the fluid being analyzed. The outer sections of the tubes are clad with a material having lower refractive indices than the tubes. A differential refractometer employing two such tube bundles and vessels is also provided. The refractometer is used as a detector in a chromatographic analyzer. The use of a coherent radiation source is stated to be particularly effective. A reference fluid is provided in one embodiment.

U.S. Pat. No. 3,619,068 describes a fiber-optics refractometer formed by a housing having two intersecting passages. The fluid to be tested is passed through the first passage, and a radiation beam is passed through the second. A bundle of light tubes is positioned in the second passage so that one end of the bundle is disposed in the test fluid at an angle with the axis of the tube bundle. A radiation detector measures the radiation passed through the tube bundle. The refractometer is particularly designed as a low-cost detector for use in liquid chromatography.

SUMMARY OF THE INVENTION

A refractive index detector comprising a waveguide, means for contacting said waveguide with a fluid, a light source and means to transmit light into said waveguide, means for detecting light exiting from said waveguide as an indication of the refractive index of said fluid and means to automatically change the angle of incidence of the light entering said waveguide in response to changes of refractive index of said fluid. A preferred embodiment of the detector for use as a detector for gradient elution chromatography has means to indicate the rate of change of refractive index. A preferred means to automatically change the angle of incidence of the light entering the waveguide is a movable prism. It is preferred to use a monochromatic light source in the detector. It is preferred to provide reference means for the detector to compensate for changes in intensity of the light output from said light source. A process for determining the refractive index of effluent from a gradient elution liquid chromatograph comprising continuously measuring the differential of the refractive index of said effluent to compensate for the change in refractive index resulting from the continuously changing composition of the elution solution.

Waveguides for use in the invention will normally be solid but can be hollow, and the fluid being analyzed can be passed around and/or through the hollow waveguides.

Waveguides can be made from transparent material such as sapphire, glass, Pyrex, quartz or other transparent inorganic material; or from transparent plastics such as polystyrene, poly-$\alpha$-methylstyrene, polymethylmethacrylate or other transparent plastic material. The waveguides can be of any convenient shape and size but for greatest sensitivity will normally be elongated in the direction of the flow of light. Cylindrical waveguides sometimes called optical fibers will normally be used; however, square, rectangular, oval or other cross-section fibers can be used.

The light source can be a commercially available light source being a substantially white light source or can be colored or substantially monochromatic in the infrared, ultraviolet, yellow, orange, green, blue or other color ranges. Monochromatic light in various colors can be supplied by light emitting diodes (LED's), and monochromatic light can be supplied by lasers.

BRIEF DESCRIPTION OF THE DRAWINGS

The invention will be more clearly understood from the following detailed description of specific examples thereof read in conjunction with the accompanying drawings wherein.

DESCRIPTION OF THE PREFERRED EMBODIMENTS

In liquid chromatography, a small volume, sensitive, universal detector is required in order to satisfy the diverse detection problems associated with this technique. The invention comprises a cell, preferably of 5 $\mu l$ volume or less; a means of passing light energy (preferably from a laser) through the cell; means of detecting said energy such as a photodiode or photomultiplier tube, amplifying the signal produced, ratioing the signal energy to a reference energy, or converting the resulting signal by appropriate means to a usable form. The variation in signal intensity is a function of the refractive index of the liquid material entering the cell. Since every material has its own distinct refractive index, this invention is capable of functioning as a catholic detector for liquid chromatography. In addition, the device can be used simply to determine the absolute refractive index of an unknown solution, either normally or automatically.

The principle of the technique is illustrated as follows: A glass rod with a refractive index higher than that of a solution to be measured is contained in a cylindrical metal holder which can be provided with means to control temperature and which functions as the cell. Provision is made for passing the liquid around the circumferential area of the rod while the ends are protected so that the liquid is contained by the inside axial wall of the cell.

Figure 1:
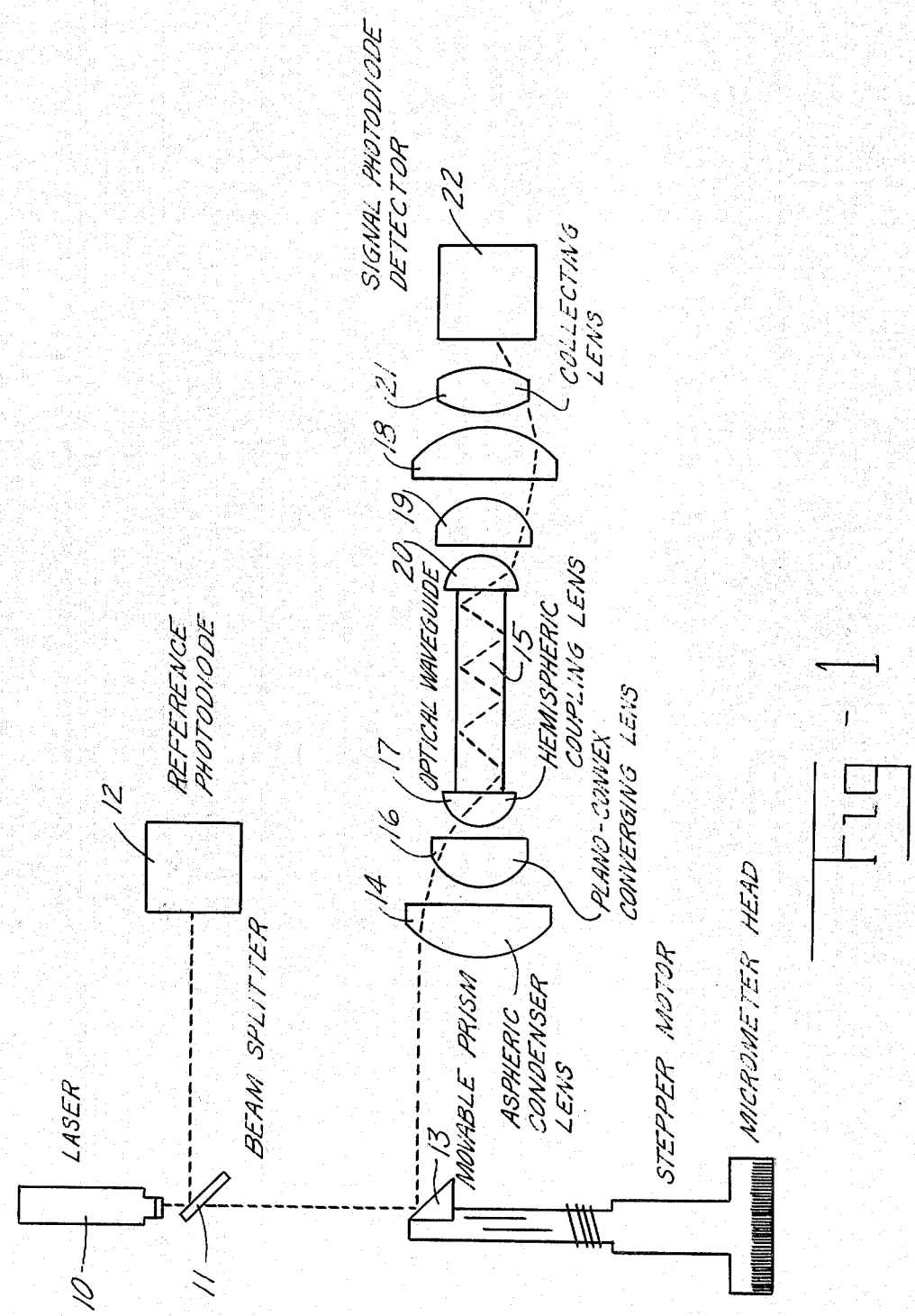
FIG. 1 is a schematic optical block diagram of the detector.

A schematic optical diagram of the instrument is shown in FIG. 1. The helium-neon laser 10 produces a diffraction limited beam of about 3 mw total power which is deflected to a reference photodiode 12 by means of the beam splitter 11. The major portion of the laser beam impinges on a movable prism 13. The prism transfers the beam to the first coverging lens 14 which focuses the beam on the front of the rod 15. Lens 16, which is a planoconvex converging lens of 10 mm FL, further bends the light so that the lower critical angles (high acceptance angles) that are necessary for measurement of low refractive index materials can be reached. Hemispheric coupling lens 17 transmits the light into rod 15. There are matching lenses 18, 19 and 20 on the exit end of the rod (waveguide), in order to maintain symmetry. Hemispheric coupling lens 17 and 18 can be glued to rod or waveguide 15, or alternatively these lens can be formed on the ends of waveguide 15 as integral parts thereof. Lens 21 is simply a signal collecting or converging lens to focus the beam on the signal photodiode 22.

Figure 2:
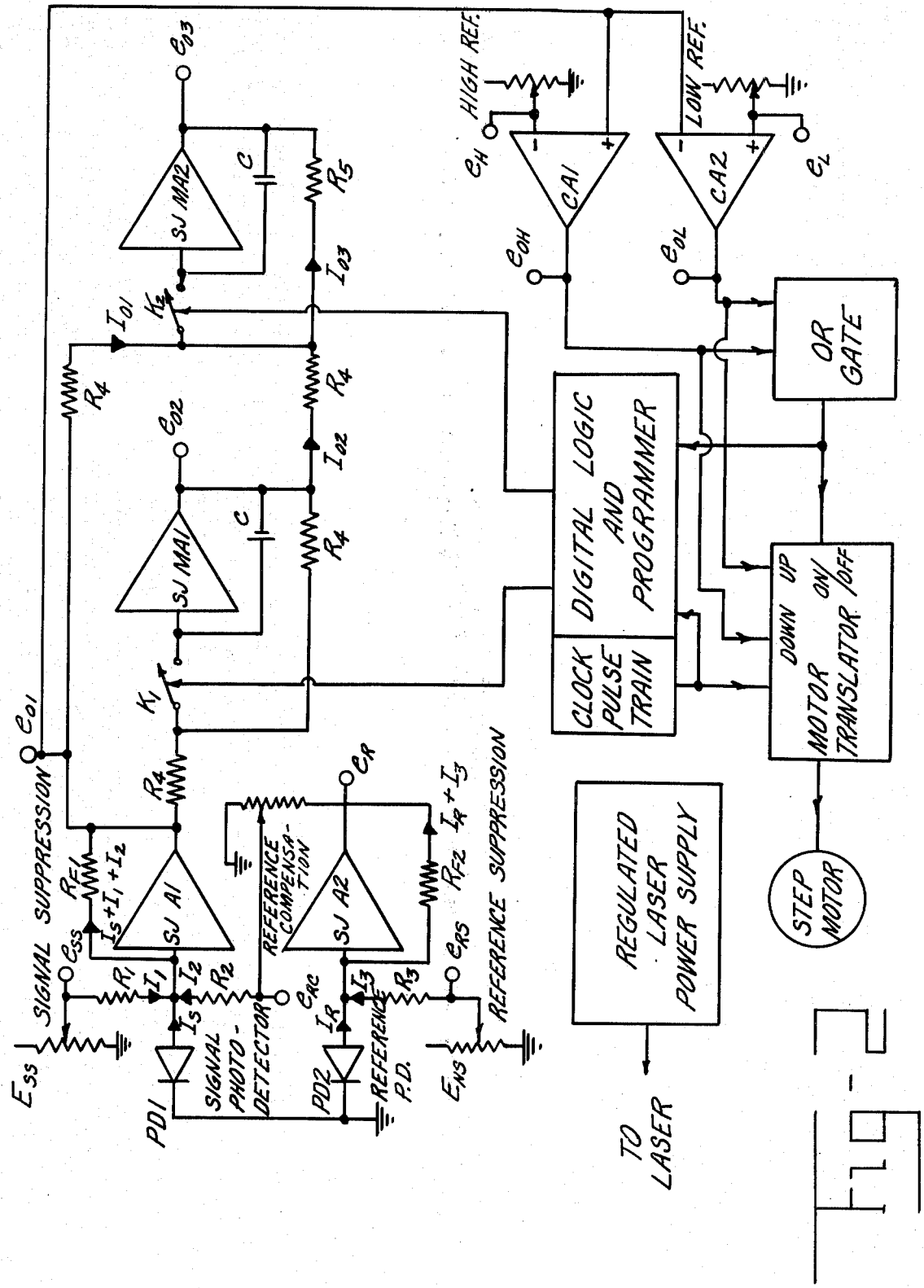
FIG. 2 is a schematic block diagram of the detector.

The electronic block diagram of the FIG. 2 shows that the instrument can function in the normal mode, in which absolute refractive index is measured, or in the differential mode. The differential mode is used primarily for gradient elution liquid chromatography, but can also be used as a detector for isocratic liquid chromatography, although the normal or non-differential mode is preferred.

A schematic optical diagram of the instrument is shown in FIG. 1. The helium-neon laser 10 produces a diffraction limited beam of about 3 mw total power which is deflected to a reference photodiode 12 by means of the beam splitter 11. The major portion of the laser beam impinges on a movable prism 13. The prism transfers the beam to the first coverging lens 14 which focuses the beam on the front of the rod 15. Lens 16, which is a planoconvex converging lens of 10 mm FL, further bends the light so that the lower critical angles (high acceptance angles) that are necessary for measurement of low refractive index materials can be reached. Hemispheric coupling lens 17 transmits the light into rod 15. There are matching lenses 18, 19 and 20 on the exit end of the rod (waveguide), in order to maintain symmetry. Hemispheric coupling lens 17 and 18 can be glued to rod or waveguide 15, or alternatively these lens can be formed on the ends of waveguide 15 as integral parts thereof. Lens 21 is simply a signal collecting or converging lens to focus the beam on the signal photodiode 22.

The electronic block diagram of the FIG. 2 shows that the instrument can function in the normal mode, in which absolute refractive index is measured, or in the differential mode. The differential mode is used primarily for gradient elution liquid chromatography, but can also be used as a detector for isocratic liquid chromatography, although the normal or non-differential mode is preferred.

Term definition for FIG. 2:
PD—PIN Diode photo detector.
$R_n$—Specific value of resistance.
$e$—Variable or signal voltage.
E—Fixed, stable voltage source.
C—Specific value of capacitance.
A—Inverting Amplifier, fixed or variable gain.
MA—Inverting operational amplifier with very high input inpedance used as a memory amplifier.
CA—Comparator Amplifier whose output is either high or low depending only on the relative value of its two input volt.
OR Gate—generates a high output voltage when either of its inputs is high.
Motor Translator—Converts a pulse train to a correct sequence to drive a stepper motor when its ON/OFF input voltage is high. The direction of rotation depends on whether the up or down input voltage is high.
SJ—Summing junction which is at virtual ground.
I—Current.

In FIG. 2, the pin diodes are operated in a shorted photo-voltaic mode. That is, the cathode is grounded and the anode is connected directly to the summing junction of an operational amplifier which is maintained at virtual ground by the feedback circuit of the amplifier. The current through the feedback resistor is the algebriac sum of all currents connecting to the summing junction. Thus, the output voltage is proportional to the sum of all input currents.

The reference detector, $PD_2$, responds only to the laser light incident on it. A reference suppression voltage, $e_{RS}$, is the source of $I_3$ which is of opposite polarity to $PD_2$ current, $I_R$. By adjusting $e_{RS}$, $I_3$ can be made equal to, but of opposite polarity, to $I_R$ such that the algebriac sum of the two currents is zero plus any variations in $I_R$. By making $R_{F2}$ large, a large voltage $e_R$, is generated which is proportional only to variations in the laser light level.

Because the amplifier, $A_2$, inverts the polarity of its intput, any current, $I_2$, derived from $I_R$ is opposite in polarity to the signal detector current $I_S$ which is proportional to the laser intensity. At any given level of $I_S$, $e_{RC}$ can be adjusted to exactly compensate for small changes in laser intensity.

The output of $A_1$, $e_{01}$, is suppressed by adjusting $e_{SS}$ to make $e_{0X}$ equal to zero at some convenient signal, $I_S$, level. Then, $e_{01}$ linearly becomes negative as $I_S$ is increased and positive as $I_S$ is decreased. $I_S$ changes if the index of refraction changes or if the motor driven prism is moved. As long as $e_{01}$ is within limits set by high and low reference voltages, $e_H$ and $e_L$, the motor remains stationary. When $e_{01}$ exceeds either $e_H$ or $e_L$, $e_{OH}$ or $e_{OL}$ becomes high, causing the motor to rotate in a direction which causes $e_{01}$ to change toward the opposite polarity. As $e_{01}$ crosses the zero volt level, the comparator is reset, causing the motor to stop. Absolute index of refraction measurements may be derived from a calibration of the vernier reading for the prism position and the output, $e_{01}$, or by the prism position alone if $e_L$ and $e_H$ are made nearly zero so that the system performance approaches that of a positioning servo system.

Figure 3:
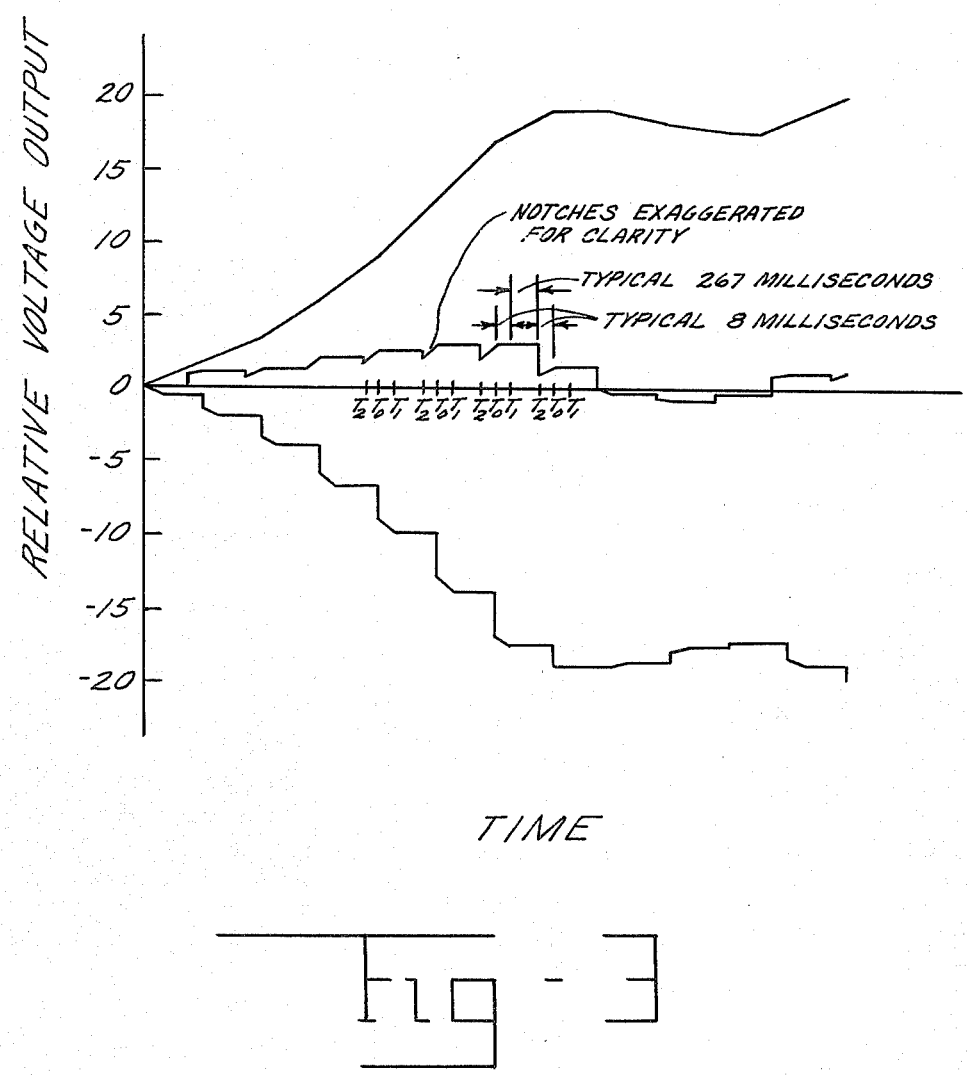
FIG. 3 is theoretical curves for an assumed signal voltage of the device.

When operating in the differential mode, the rate of change of index of refraction is measured by programming the memory amplifier switches, $K_1$ and $K_2$, as follows (see FIG. 3). At time $T_0$, $K_1$ closes causing $e_{02}$ to assume a value, $e_{02} = -e_{01}@T_0 < t < T_1$. That is, $e_{02}$ becomes the negative of $e_{01}$ from time $T_0$ to $T_1$. At time $T_1$, $K_1$ opens leaving $e_{02} = -e_{01}@T_1$. At time $T_2$, $K_2$ closes causing $e_{03}$ to assume a value, $e_{03} = -(R_5/R_4)(e_{01} + e_{02})@T_2 < t < T_0$. That is, $e_{03}$ becomes the negative of the sum of $e_{01}$ and $e_{02}$ from time $T_2$ to time $T_0$ which starts a new cycle. Then, at $T_0$, $e_{03} = -(R_5/R_4)(e_{01}@T_0 - e_{01}@T_1)$ which is proportional to the change in $e_{01}$ from time $T_1$ to time $T_0$ which is a fixed time interval. Therefore, $e_{03}$ is directly proportional to the rate of change of the signal current, $I_S$.

In summary, $e_{01}$ is an analog voltage signal which varies linearly with the light incident on the signal detector, $PD_1$. $e_{01}$ is bipolar and becomes negative as the light intensity increases from some mid value and becomes positive as the light intensity decreases below the mid value. $e_{02}$ is updated periodically and is equal but opposite in polarity to $e_{01}$ at the point in time $e_{02}$ was last updated. $e_{03}$ is proportional to the change in $e_{01}$ over a fixed, but programable, period of time. It is negative for an increasing $e_{01}$ and positive when $e_{01}$ is decreasing.

Figure 4:
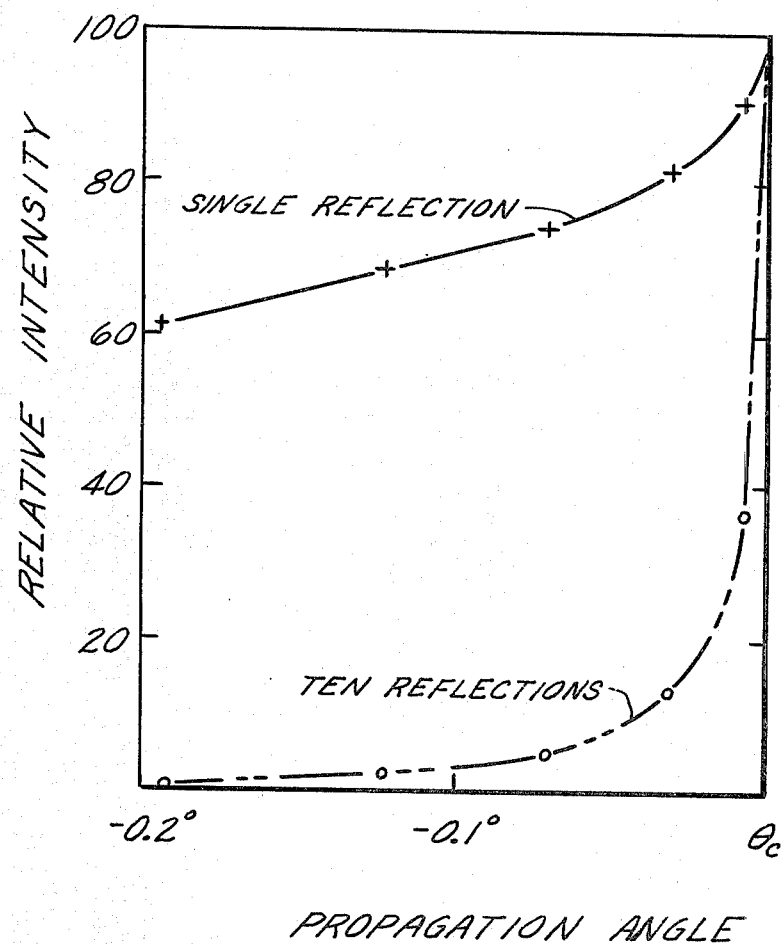
FIG. 4 shows the effect of multiple reflections in the waveguide of the invention.

In order to measure refractive index, we make use of the fact that light rays entering the rod at angles larger than the critical angle $\theta_c$ are internally reflected, while those entering the rod at angles less than the critical angle leave the system. The ability to accurately detect differences in refractive index can be enhanced by producing multiple reflections in the rod. This is shown in FIG. 4. The number of reflections for a 2 cm rod of 1 mm diameter is as follows.

| $\theta_A$ (acceptance angle) | No. of Reflections for a 2 cm Rod of 1.675 RI |
|---|---|
| 10° | 1.25 |
| 20° | 4.17 |
| 30° | 6.26 |
| 40° | 8.31 |
| 50° | 10.29 |
| 60° | 12.08 |
| 70° | 13.55 |

As the acceptance angle is varied and the critical angle is passed, the light reaching the detector goes from a very high value to a low value, or vice versa, depending upon the direction of approach. This can be made to happen over a very short range of refractive index, depending upon the amount of gain set on the input amplifier. The curve obtained is shown in FIG. 5 for a single setting of the prism, and as the prism setting is changed a family of similar curves is obtained displaced horizontally as compared to the curve shown.

Figure 5:
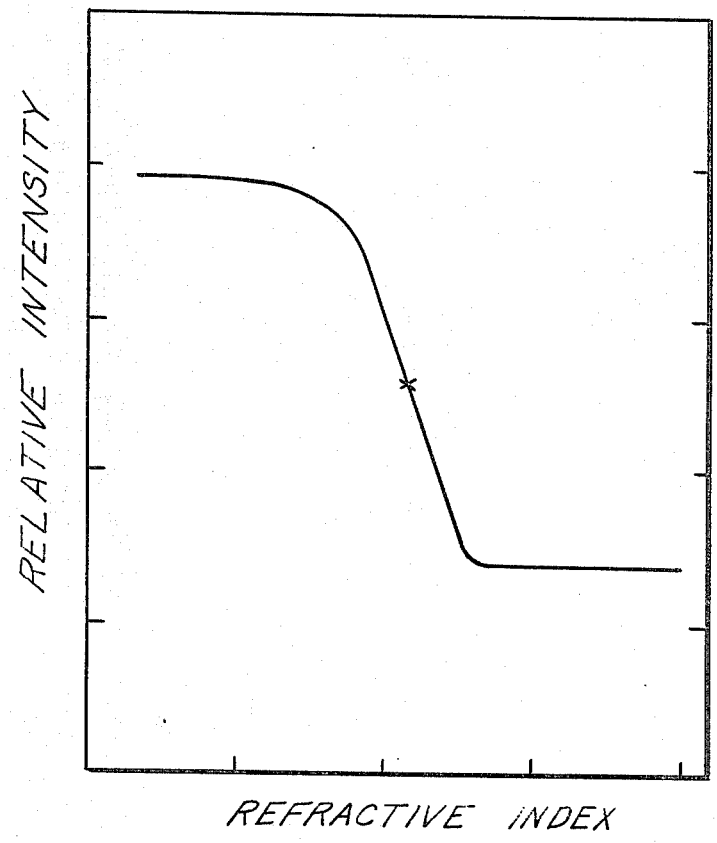
FIG. 5 is illustrative of one of the family of curves obtainable using the detector of the invention.
Figure 6:
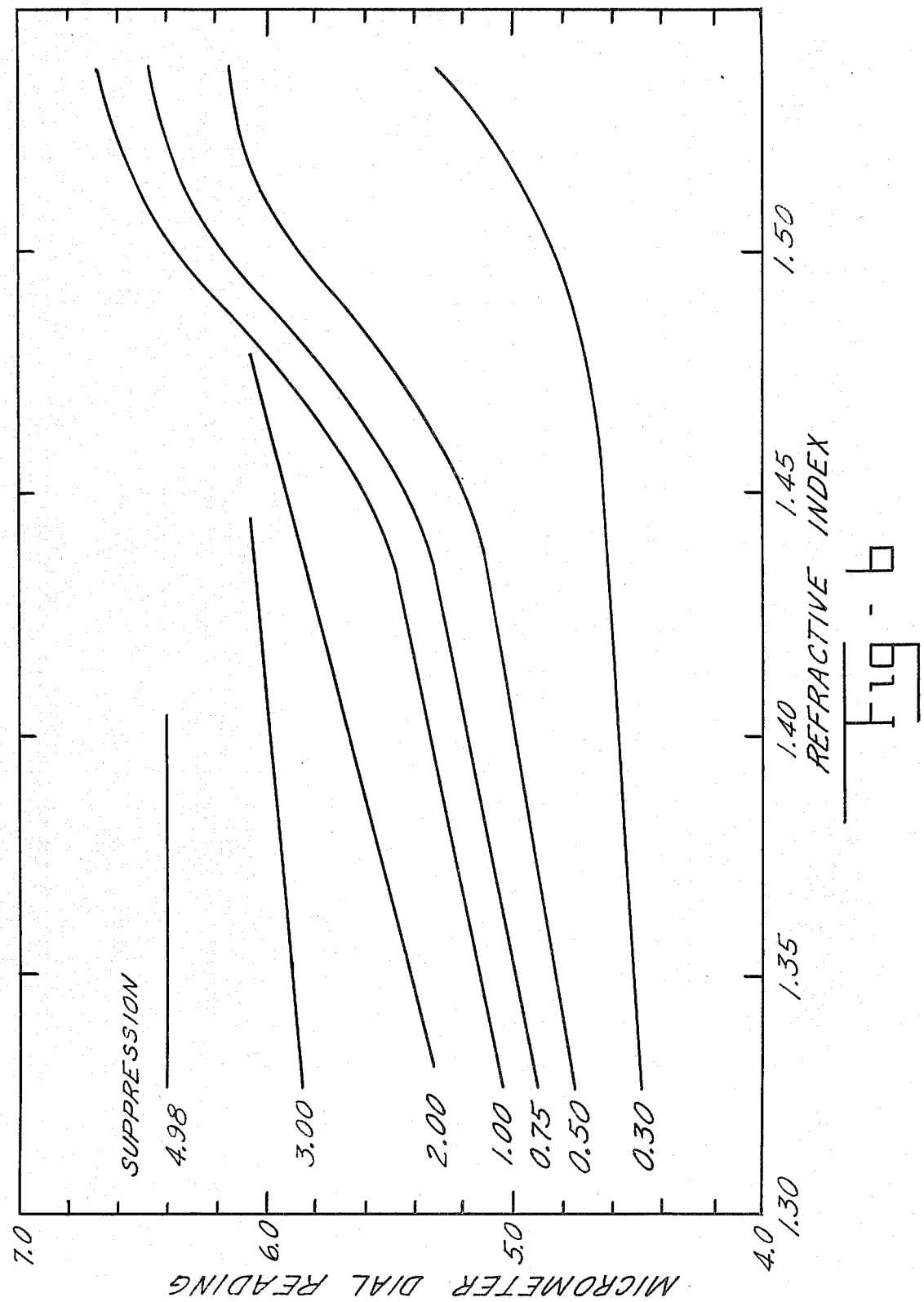
FIG. 6 shows a family of curves obtained using a detector of the invention showing refractive index vs. micrometer dial reading at various suppression settings.
Figure 7:
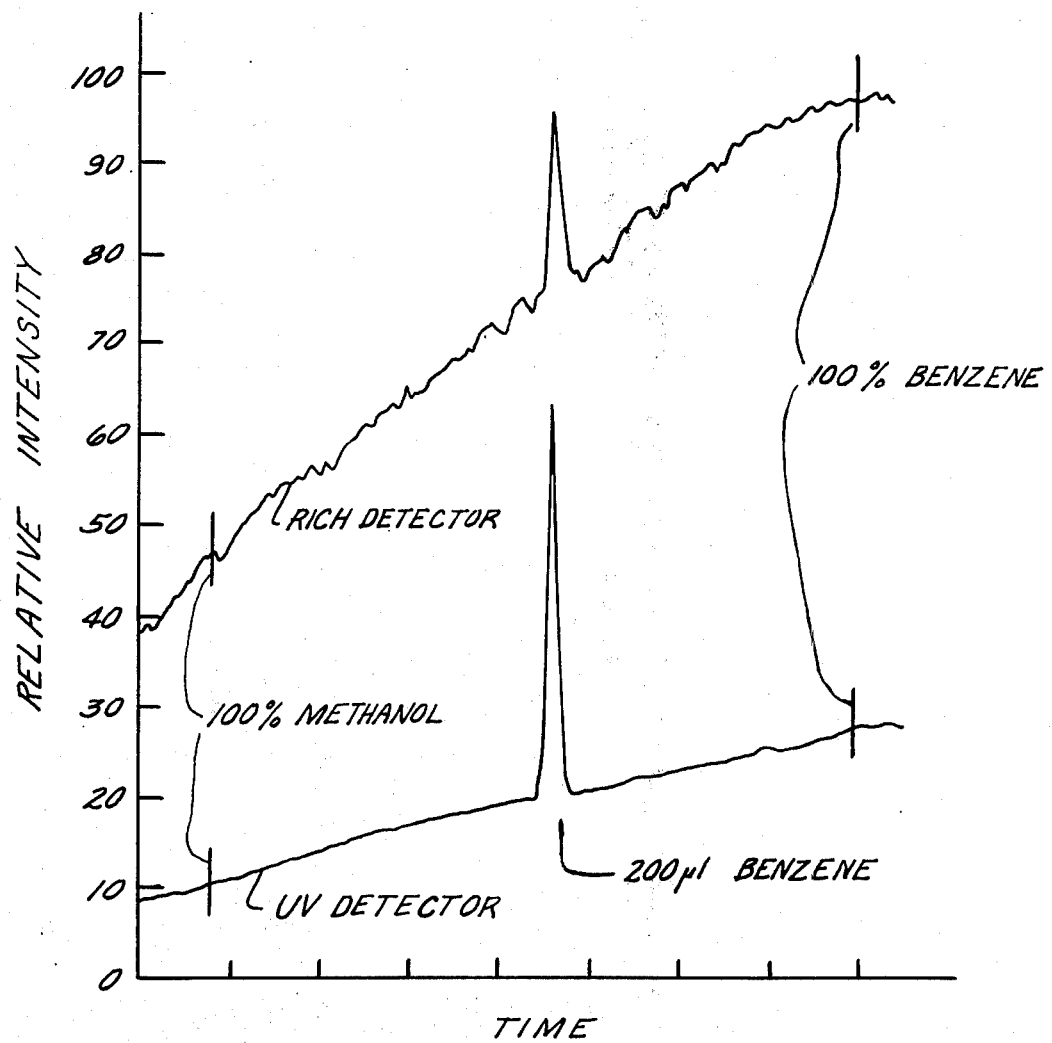
FIG. 7 is an illustrative comparison of data obtainable using a Variscan UV Detector compared with a detector of the invention when operating in the absolute (non-differential) mode on effluent from a gradient elution chromatograph with both detections in series.
Figure 8:
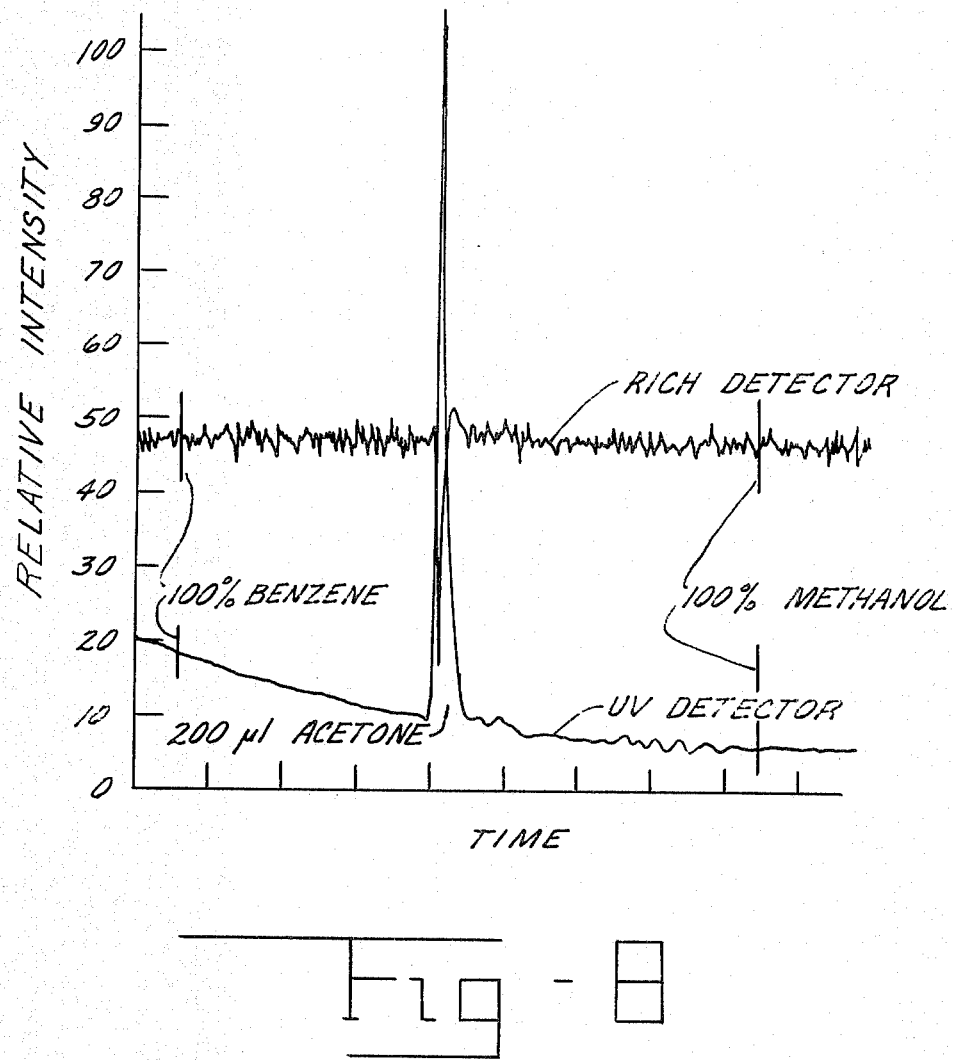
FIG. 8 is an illustrative comparison of data obtainable using a Variscan UV Detector compared with a detector of the invention when operating in the differential mode on effluent from a gradient elution chromatograph with both detectors in series.

In the normal mode, suppression is applied to the input amplifier $A_I$ (FIG. 2) so that its output is somewhere on the response/RI curve, say point X (FIG. 5). In this mode the device is acting as a null detector. Any change in refractive index causes a different light level to fall on the photodiode which raises or lowers the DC level to the input amplifier. Since this amplifier's output serves as the input to the two comparison amplifiers, $CA_1$ and $CA_2$, any change at this point causes the stepper motor to drive the movable prism and the integral micrometer dial back to the null position. The refractive index can then be read directly from the dial. The curves of refractive index vs micrometer dial readings for various amounts of suppression are shown in FIG. 6.

The differential mode utilizes the memory amplifiers, $MA_1$ and $MA_2$, and is used for conditions which one encounters in gradient elution work. Here, it is desired to measure components of one refractive index that are present in a mixture of solvents whose refractive index is both different from that of the component of interest, and varies with time according to some prescribed conditions.

The stepper motor, which has a resolution of 200 steps per revolution, will advance or retard the prism at a rate consistent with absolute changes in refractive index of the solvent system. A constantly changing system will produce a derivative signal of a constant, unless a component is present that results in a change of rate that produces an output of amplifier $MA_2$ proportional to this change.

Figure 9:
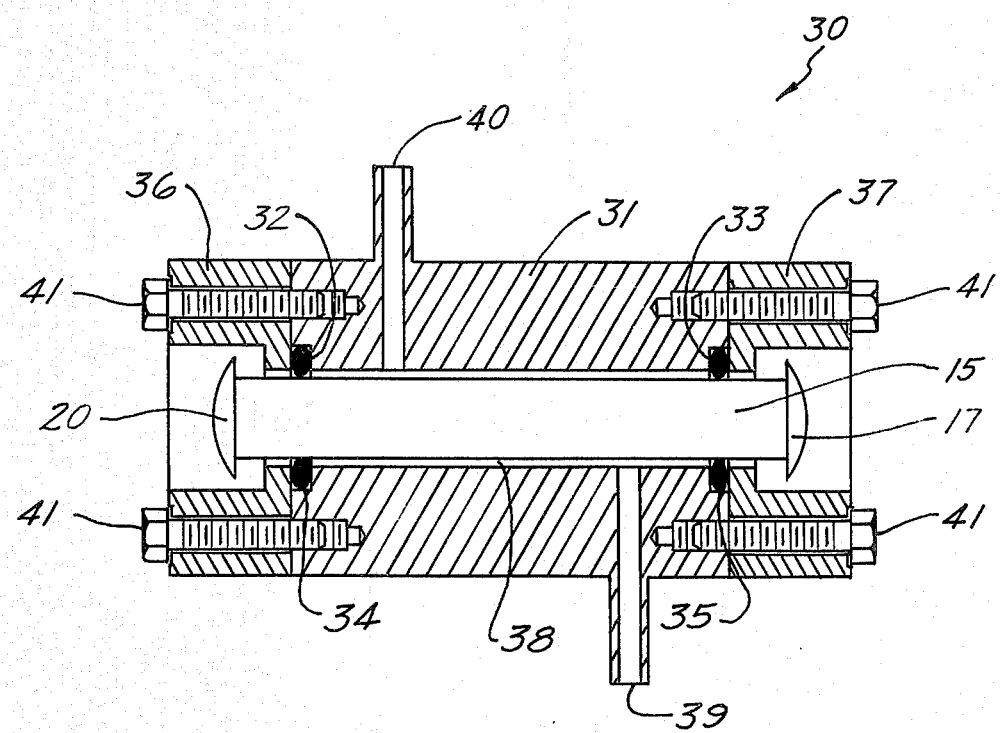
FIG. 9 is a sectional view of a cell for holding the waveguides.

FIG. 9 shows a cell 30 for holding the waveguides of the invention. Cell 30 is made up of metal body 31, suitably stainless steel, having notches 32 and 33 for receiving 0-rings 34 and 35, suitably silicon rubber. Flanges 36 and 37, suitably stainless steel, are bolted to body 31 by bolts 41. Waveguide 15 (see FIG. 1), suitably glass, havng hemispherical coupling lens 17 and 20, suitably glass, are glued to the ends of waveguide 15. Flanges 36 and 37 when tightened against body 31 by bolts 41 press against 0-rings 34 and 35 forming a seal between waveguide 15, flanges 36 and 37 and body 31 providing an annular space 38 around waveguide 15 to contain liquid sample being analyzed. Inlet pipe 39 is used to add sample for analysis to annular space 38 and outlet pipe 40 allows removal of sample from annular space 38. Heating, cooling and temperature control by conventional means can be provided for through cell 30 to control the temperature of the sample being analyzed.

Advantages of the invention are as follows:

1. Provides a sensitive and simple way of detecting and measuring the presence of materials in the effluent of a liquid chromatograph.

2. Automatically indicates if the component has a higher or lower refractive index than the solvent and thus gives diagnostic information.

3. Provides a low volume cell of 5 µl or less.

4. Can be used to accurately measure the absolute refractive index of an unknown solution.

5. Can automatically track and measure the changing refractive index of solution through a unique null detection principle.

6. Allows continuous refractive index monitoring when operated in a flow through mode.

7. Because of a unique differential operation principle, the device can measure the presence of a component in solution whose refractive index itself is varying.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What we claim is:

1. In a refractive index detector comprising an elongated waveguide, means for contacting said waveguide with a fluid, a light source and means to transmit light into said waveguide and means for detecting light exiting from said waveguide as an indication of the refractive index of said fluid, the improvement comprising means to automatically change the angle of incidence of the light entering said waveguide in response to changes of refractive index of said fluid.

2. A detector of claim 1 wherein means are provided to indicate the rate of change of refractive index.

3. A detector of claim 1 wherein said means to automatically change the angle of incidence of the light entering said waveguide is a movable prism.

4. A detector of claim 1 wherein said light source is monochromatic.

5. A detector of claim 1 wherein reference means are provided to compensate for changes in intensity of the light output from said light source.

6. A refractive index detector comprising an elongated waveguide, means for contacting said waveguide with a fluid, a monochromatic light source and means to transmit light into said waveguide, means for detecting light exiting from said waveguide as an indication of the refractive index of said fluid, movable prism means to automatically change the angle of incidence of the light entering said waveguide in response to changes in refractive index of said fluid and reference means to compensate for changes in intensity of the light output from said light source.

7. A refractive index detector comprising an elongated waveguide, means for contacting said waveguide with a fluid, a monochromatic light source and means to transmit light into said waveguide, means for detecting light exiting from said waveguide as an indication of the refractive index of said fluid, movable prism means to automatically change the angle of incidence of the light entering said waveguide in response to changes of refractive index of said fluid, means to indicate the rate of change of refractive index and reference means to compensate for changes in intensity of the light output from said light source.

* * * * *